United States Patent [19]

Schneider

[11] Patent Number: 4,815,816
[45] Date of Patent: Mar. 28, 1989

[54] IMAGE TRANSPORTATION DEVICE USING INCOHERENT FIBER OPTICS BUNDLES AND METHOD OF USING SAME

[75] Inventor: Richard T. Schneider, Alachua, Fla.

[73] Assignee: RTS Laboratories, Inc., Alachua, Fla.

[21] Appl. No.: 48,815

[22] Filed: May 12, 1987

[51] Int. Cl.⁴ ............................ G02B 6/06; H01J 5/16; A61B 1/06

[52] U.S. Cl. .................... 350/96.25; 350/96.24; 350/320; 350/96.18; 350/507; 350/540; 350/96.26; 250/227; 128/4; 128/6

[58] Field of Search .............. 350/96.10, 96.18, 96.24, 350/96.25, 96.26, 320, 507, 540; 128/4, 6; 250/227

[56] References Cited

U.S. PATENT DOCUMENTS

| | | | |
|---|---|---|---|
| 2,992,587 | 7/1961 | Hicks, Jr. et al. | 350/96.25 |
| 3,128,167 | 4/1964 | Woodcock | 350/96.25 X |
| 3,464,330 | 9/1969 | Lewis | 350/96.24 |
| 3,512,861 | 5/1970 | Schackert | 350/96.25 |
| 3,556,085 | 1/1971 | Takahashi | 350/96.26 |
| 3,652,855 | 3/1972 | McIntyre et al. | 250/227 X |
| 3,669,524 | 6/1972 | Shio | 350/96.25 |
| 3,814,081 | 6/1974 | Mori | 350/96.26 X |
| 3,933,409 | 1/1976 | Kloots | 350/96.20 X |
| 3,933,455 | 1/1976 | Chown | 350/96.20 X |
| 4,076,378 | 2/1978 | Cole | 350/96.24 |
| 4,275,950 | 6/1981 | Meyer | 350/96.10 |
| 4,332,439 | 6/1982 | Lubbers et al. | 350/320 |
| 4,570,063 | 2/1986 | De Bie et al. | 250/227 |
| 4,674,834 | 6/1987 | Margolin | 350/96.25 |
| 4,702,552 | 10/1987 | Margolin | 350/96.25 |
| 4,738,510 | 4/1988 | Sansom | 350/96.25 |
| 4,760,421 | 7/1988 | Margolin | 350/96.25 X |
| 4,762,391 | 8/1988 | Margolin | 350/96.25 |

FOREIGN PATENT DOCUMENTS

| | | | |
|---|---|---|---|
| 3226015 | 1/1984 | Fed. Rep. of Germany | 350/96.25 |
| 1533123 | 6/1968 | France | 350/340 |
| 58-100813 | 6/1983 | Japan | 350/340 |

Primary Examiner—William L. Sikes
Assistant Examiner—Brian M. Healy
Attorney, Agent, or Firm—Foley & Lardner, Schwartz, Jeffery, Schwaab, Mack, Blumenthal & Evans

[57] ABSTRACT

The invention includes a fiber optic bundle comprising a plurality of individually optic fiber elements. Each of the optic fiber elements has a first end and a second end. The first ends of the optic fiber elements have a smaller cross-sectional area than the second ends. The first ends are mechanically joined to provide strength to said fiber optic bundle. Detectors are connected to the second ends for receiving light channeled through the optic fibers. Due to the increase in size of the optic fibers from the first end to the second end, a magnification in the transported image takes place.

16 Claims, 3 Drawing Sheets

DRAWN AFTER FUSING

DRAWN BEFORE FUSING

SUB BUNDLES

MASK

GAGE FOR SETTING WALLS OF FRAME

FIBER MICROSCOPE

PERISCOPE

INSECT EYE

IMAGE TRANSPORTATION DEVICE USING INCOHERENT FIBER OPTICS BUNDLES AND METHOD OF USING SAME

The U.S. Government has a paid-up license in this invention and the right in limited circumstances to require the patent owner to license others on reasonable terms as provided for by the terms of contract No. N00014-85-C-0862 awarded by the Dept. of the Navy.

BACKGROUND OF THE INVENTION

1. Field of the Invention

The present invention relates to fiber optic bundles for transporting images, and especially to such fiber optic bundles which have a high image resolution.

2. Discussion of Related Art

With the advent of fiber optics technology, the opportunity of transporting optical images in fiber bundles became available. Such bundles conventionally have a point-to-point relation between the input and the output of the fiber bundle. Such bundles are called "coherent bundles" and are in widespread use, e.g. in fiberscopes, etc.

There are, however, certain shortcomings which need to be overcome. These relate to the size of the input and output area of the bundle and the diameter of the individual fibers used in the bundle.

Since in a coherent bundle, the location of each fiber has to be identical in the input and output plane, it becomes more and more difficult to keep track of each fiber because as the image area becomes larger the total number of fibers is increased.

Further, in any fiber bundle, the diameter of the individual fibers determines the resolving power of the system. The smaller the diameter, the better the resolving power. The maximum acceptable diameter depends on the application. However, at the same time, the smaller the diameter of the optic fiber, the weaker the fiber. If the fiber becomes too small, it is difficult if not impossible to handle without damage.

The resolution of an image can be expressed in line pairs/mm. For example, if a resolution of 100 line pairs/mm is needed, and if at least 4 fibers were required per line pair, then a fiber diameter of $1/400$ mm = 2.5 micrometers would be required. A resolution of 100 line pairs/mm is achievable with photographic film. Standard fibers are 50 micrometers; therefore, they produce a resolution of about 5 line pairs/mm. A 50 micrometer fiber is barely visible with the naked eye. Photographic emulsions using this size grain would not be considered acceptable. In principle, glass fibers could be drawn out to 2.5 micrometer diameter, but the mechanical strength would be so low that handling of such a bundle would be very difficult, at the least.

If a fiber optic bundle is to compete in resolution with a 35 mm camera, $36 \times 400 = 14400$ fibers per image line are required for a total of $24 \times 400 = 9600$ image columns or $1.4 \times 10^8$ fibers altogether. If a fiber optic bundle is to compete in resolution with a large sheet film, e.g., chest x-ray (maybe $10 \times 10$ in.), on the order of $10^{12}$ fibers are required. These are, of course, fantastic numbers, but they illustrate the basic problem.

In view of the foregoing problems, it can be seen that it is not always feasible to compete with a 35 mm camera. However, several scenarios exist where fiber optic bundles can replace cameras. For example, if pictures are to be taken in high radiation environments, e.g. inside a throughport of a nuclear reactor, photographic recording is impossible. One could transport the image with relay lenses to a low radiation area and then take the picture photographically, or one can use a fiber optics bundle for transportation of the image. Fibers which are radiation hardened are available for such an application. Therefore, in this case one indeed competes with photographic recording. The fiber optics cable can be snaked around corners, while the relay lenses need a clear aperture, giving range to shielding problems. Therefore, a fiber optic bundle would indeed be preferable if it could deliver the required resolving power. The same argument is true for any other periscope arrangement, e.g., for a submarine. Here, also, it would be advantageous to replace the relay lenses by a fiber optics bundle; however, the resolving power cannot be compromised.

Any application where observation of inaccessible locations are attempted, the fiber optics bundle is preferable. If the location is so inaccessible that an optical relay is not possible, one does not compete with the photographic camera anymore, therefore, any resolving power is welcome. If a relay is possible, one has to be able to offer a resolving power comparable to the photographic camera. Thus, it can be seen that a need has developed for a fiber optic device capable of transporting high resolution images.

Various fiber optic bundles have been suggested. For example, Wilcox (U.S. Pat. N0. 3,461,223) uses an ordered fiber array which is electronically scanned. It is intended for color television images. The actual image transmission is accomplished by air (UHF) or electrical cable. The fiber array is a decoding and encoding means only, not a transmission means.

Schackert (U.S. Pat. No. 3,512,861) uses a single row or a limited number of rows of ordered fibers which are mechanically moved to achieve scanning. Image transmission is through one row (or few rows) of ordered fibers.

McIntyre (U.S. Pat. No. 3,652,855) uses an ordered fiber optics bundle connected to a limited number (70) of photomultiplier tubes. An elaborate coding scheme between the input fibers and the photomultiplier tubes, together with a coincidence circuitry, allows obtaining of more than 70 pixels. The fiber bundle used is short and ordered. The coding scheme is specified in greater detail in a successive patent (McIntyre, U.S. Pat. No. 4,379,967).

Schaefer (U.S. Pat. No. 4,052,705) describes actually a memory device for computers. One could construe that it constitutes the transport of images. However, the bundles (mostly one rowers) are strictly ordered and short. They are used to form various types of gates (and, or, not, etc.).

The patent to DeBie (U.S. Pat. No. 4,570,063) also a discloses a one row device which is meant for scanning a document.

There is no known structure suitable for transporting high resolution images through fiber optics.

SUMMARY OF THE INVENTION

One object of the present invention is to provide a fiber optic bundle which is capable of transporting high resolution images.

Another object of the present invention is to provide a fiber optic bundle which is rugged and can be handled without fear of damage.

A further object of the present invention is to provide a fiber optic bundle which can be manufactured inexpensively using randomly oriented fibers, and a system for descrambling the output of the optic bundle to provide a coherent image.

Another object of the present invention is to provide a method of producing a fiber optic bundle capable of transporting a high resolution image.

In accordance with the above and other objects, the present invention is a fiber optic bundle comprising a plurality of individual optic fiber elements, each of which has a first end and a second end. The first ends of the optic fiber elements are of a smaller cross sectional area than the second ends and are mechanically joined together to a fiber optic bundle in order to provide sufficient strength. A detector array is connected to the second ends of the optic fibers for receiving light which is transmitted through the fibers from the first ends of the optic fibers.

The second ends of the optic fiber elements may be joined together into sub-bundles having at least one optic fiber each, but typically will consist of several thousand fibers. One detector array may be connected to each sub-bundle. An optical mask may be connected to the fibers for mating individual fibers of the sub-bundles to individual detectors on the optical detector array.

The first end of each optic fiber may be at least as small as about 5 micrometers in diameter and the second end of each optic fiber may be at least as large as about 50 micrometers in diameter.

The second end of each optic fiber may at least an order of magnitude greater in diameter than the first end.

The location of the first ends of the optic fibers on the input plane may be arranged randomly relative to the location of the second ends on the output plane, and therefore there may be included a system for descrambling light signals received from the second ends to produce a correct image of an image projected onto the first ends.

The descrambling system may comprise a computer program relating the addresses of the input (first) ends to the addresses of the output (second) ends and the necessary hardware to display the reconstructed image on a monitor. "Address" is here defined as the cartesian coordinate of an individual fiber on the input or output plane.

The present invention also includes a method which comprises providing a plurality of optic fibers, each having a first end and a second end; mechanically joining together the first ends of the optic fibers to form a fiber bundle; and reducing the cross section of the first end of each optic fiber relative to its second end.

The step of reducing the cross section of the first ends of the optic fibers may comprise reducing the cross section of each optic fiber individually before connection to form the bundle.

Alternatively, the step of reducing the cross section of the first ends of the optic fibers may comprise reducing the cross section of all of the optic fibers together after they are joined together to form the bundle.

BRIEF DESCRIPTION OF THE DRAWINGS

The above and other objects of the present invention will become more readily apparent when the invention is more fully understood from the detailed description to follow, reference being had to the accompanying drawings, in which like reference numerals represent like parts throughout, and in which.

DETAILED DESCRIPTION OF THE PREFERRED EMBODIMENTS

The present invention includes fiber optic bundles having fibers with diameters which are sufficiently small to permit the transmission of high resolution images by such bundles. Therefore, before discussing the construction of the invention, discussion of what constitutes a suitable fiber diameter for use in the invention will be set forth.

In order to transmit an image through an optic bundle, one would illuminate the input plane of the bundle with a conventional optical system, e.g., a lens, in a way that a sharp image falls on said input plane. The wavelength of the light used and the diameter of the lens used determine the angular resolving power. Regardless of this, the linear resolving power, namely the diameter of the Airy disk, cannot be smaller than the order of magnitude of the wavelength of the light used. In the case of visible light we may approximate this by 0.5 micrometer. Considering lens imperfections, 2.5 micrometers is a good value for an achievable Airy disk. The resolving power of the human eye in the fovea is considered to be 5 micrometers which translates to about 100 micrometers at reading distance (400 mm). Therefore, for an instrument used for visible observations, 50 micrometer resolution would be good enough. However, to transport an image obtained by a telescope (10×), 5 micrometer fiber diameter would be required. In other words, a fiber diameter in the 5–8 micrometer range would be a reasonable diameter to meet existing requirements. Consequently, for 35 mm format (24×36 mm), a bundle containing about $3.5 \times 10^7$ fibers would be required.

If one had a fiber bundle of such a size one could take a photographic image of the exit plane of the bundle and could expect to obtain about the same quality as if the camera had been located in the entrance plane of the bundle. However, for some applications it is preferable to replace the photographic film by a detector array.

The present invention includes a fiber optic bundle of random orientation of the fibers. By allowing the fibers to be randomly oriented, any size bundle of any length can be easily assembled from standard 50 micrometer fibers. Of course, with such a bundle, the image will appear to be "scrambled" at the output end of the fiber. The present invention also includes a computerized procedure to unscramble the image.

Figure 1:
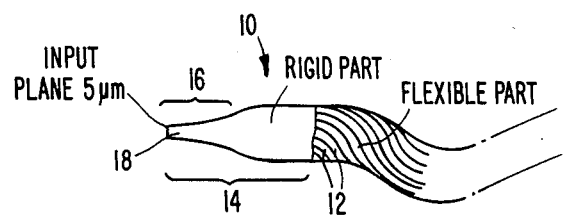
FIG. 1 shows a fiber optic bundle according to the present invention produced by drawing the bundle after fusing the fibers.

The fibers themselves are made to be 50 micrometers in diameter. These fibers are cemented together at the input end of the bundle for a short length only. The so-formed rigid part is drawn out using a suitable amount of heat until the diameter of the bundle is reduced by a factor of 10 at the input end. A fiber bundle 10 is shown in FIG. 1 having a plurality of fibers 12 connected together for a predetermined length 14. The connected fibers have been drawn down to the desired size in the region 16. The fibers having the smallest cross sectional area form the input end 18 of the bundle. The individual fibers at the opposite end of the bundle are separate from one another.

Figure 2:
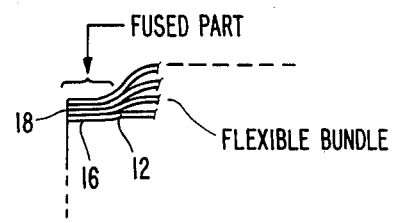
FIG. 2 shows a fiber optic bundle according to the present invention being produced by drawing the fibers before fusing.

It is noted that in the structure shown in FIG. 1, the fibers were connected first and then drawn down to size. An alternate method is shown in FIG. 2 in which each individual fiber 12 is drawn until its end 16 is down to 5 micrometers during the manufacturing process. The ends are then cemented together to form the input plane.

If silica glass fibers are used, the drawing process is well known technology. If plastic fibers are used, a butt joint is used between the polished end of the 50 micrometer plastic fiber bundle and a short rigid conical piece of a drawn out (drawn from 50 to 5 micrometers) silica glass fiber bundle.

It should be understood that the individual 5 micrometer fibers are fragile and difficult to handle without damage. Accordingly, the connection of these fibers to one another enhances the strength of the individuals and enables them to be easily handled. Also, by maintaining the 50 micrometer size of the output ends of the fibers and not connecting these larger ends to one another, the connection of the fiber bundle to a detector array is facilitated, as discussed below. Thus, the invention has the flexibility and the mechanical strength of 50 micrometer diameter fibers as well as the resolving power of 5 micrometer fibers.

Figure 3:
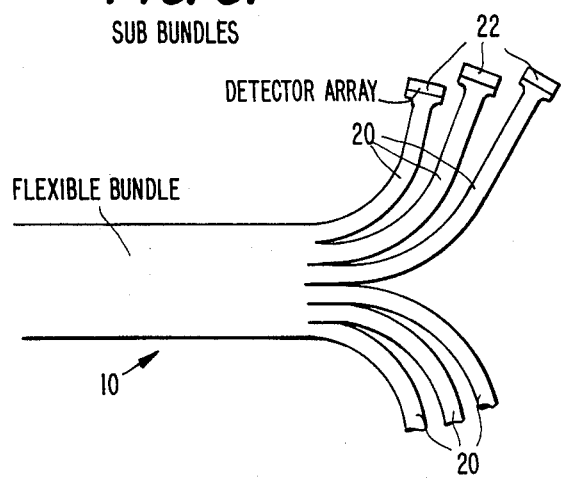
FIG. 3 shows a fiberr optic bundle according to the present invention connected to a plurality of detectors on a detector array through a plurality of masks.

The detector interface will now be discussed. First, the output ends of the fibers in the bundle may be divided into sub-bundles 20 as indicated in FIG. 3. Each sub-bundle may contain one or more fibers (typically several thousand) and is connected to a detector array 22. The output end of each fiber bundle still consists of 50 micrometer diameter fibers. The number of fibers per sub-bundle will be equal to the number of detectors available on a detector array chip 22 (e.g., 256×512). In this case, a bundle containing $3.5 \times 10^7$ fibers at the input end is subdivided for connection to about 260 detector array chips. The size of each individual detector on the array may be 50 micrometers in diameter, which is easier to manufacture than a 5 micrometer diameter detector. The separation between detectors on the array chip may be of any size; however, for reasons which will become apparent below, it is preferred that this dimension also be 50 micrometers.

Figure 4:
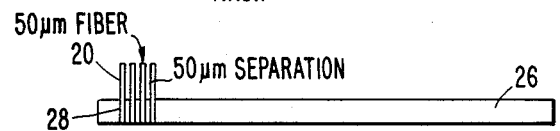
FIG. 4 shows a mask for use with a fiber optic bundle according to the present invention.

Masks containing 50 micrometer holes (or slightly larger) are produced for attaching a fiber bundle to a detector array chip 22. One such mask 26 is shown in FIG. 4 having a plurality of 50 micrometer holes 28 for receiving the 50 micrometer fiber ends 20. The individual fibers in the output ends of the sub-bundles are fed into the holes 28 of the mask 26 and cemented in place as indicated in FIG. 4. After polishing, the mask is aligned with detector array chip 22 so that each fiber end 20 is opposite an individual detector. The alignment is accomplished by illuminating the input end 18 of the total bundle homogeneously and checking for maximum signal output of the detector array.

It is assumed that no space restriction exists at the output end. Nevertheless, the output end (including dead space) should not be larger than a factor of 20 times the size of the input end. Therefore, the 36 mm input end dimension would grow into a 70 cm output end dimension.

As will be understood from the foregoing discussion, despite the fact that the output ends of the fibers are 50 micrometers each, the resolving power of the bundle is still 5 micrometers. A bad detector (50 micrometer), therefore, results in a loss of a 5 micrometer pixel.

Descrambling of the signals at the output end is accomplished by projecting a family of curves onto the input end of the total bundle. The curves may form an orthogonal grid with reasonable spacing. The grid spacing can be varied at successive projections, or the lines may be just shifted and the grid spacing may be kept constant. In either case, the intersection of a vertical line and a horizontal line defines a pixel of the overall image, and also constitutes the address of the underlying fiber. The output end of each individual fiber is connected to one certain detector. The address of this detector is determined by illuminating one pixel only on the input plane of the fiber bundle. Pixel addresses and the corresponding detector addresses are stored in pairs to form a look-up table to "translate" a scrambled image received by the detector array into the original image as it appeared on the input plane. This look-up table is, of course, different for each bundle manufactured and is therefore to be provided to the user along with the cable.

The manufacturing of the mask shall now be described. In principle, 50 micrometer holes (about 2 thousandths of an inch) can be drilled in a plate on a numerically controlled (NC) machine tool to form a mask. While this procedure may be adequate for producing prototypes, the sheer number of holes would make this a very expensive operation for the mass production of masks, even for a NC machine. Therefore, it is preferable to cast the mask, rather than machine it. The material used for casting could be a polyester or epoxy. It should be black and it should not shrink. Also, it should have good long-term stability. There are several materials available which meet these requirements.

Figure 5:
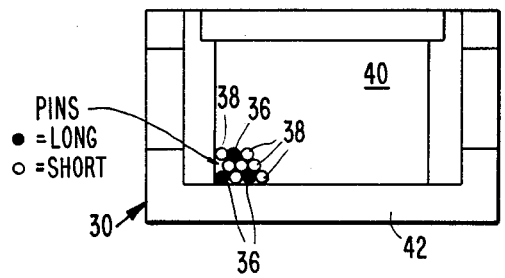
FIG. 5 shows a top plan view of a mold for producing a mask according to the present invention.
Figure 7:
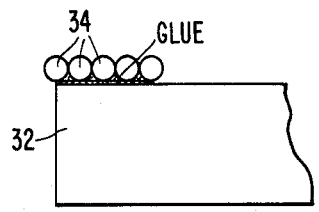
FIG. 7 shows a gage for setting the walls of the mold of FIGS. 5 and 6.

The mold required for the casting is constructed as follows. A set of cylindrical steel pins about 1 inch long and another set of cylindrical steel pins ¾ inch long, all having a diameter of 0.002 in., are required. The total number of pins in each set is four times the number of fibers to be mated to the detector chip. Then a frame 30 as shown in FIG. 5 is manufactured. The frame has to be precision machined, so that exactly 1024 pins (for a 512 detector row) fit to whatever tolerance they may have. The fitting procedure is as follows. A slightly undersized slab 32 is machined as shown in FIG. 7 and one row of 1024 one-inch long pins 34 is glued onto it. Care has to be taken that the glue is spread sufficiently thin that it does not get between the pins. Rotation of the pins has to be avoided during the gluing process. Once the glue has set on the slab, this assembly serves as a gauge to machine the sides of the frame shown in FIG. 5 so that it will accept exactly 1024 pins. Once the frame has been adjusted, one row comprising pins 36, 0.002"

in diameter and 1" long alternating with pins 38, 0.002" in diameter and ¾" long, is glued into it. After the glue has set, another row of pins 36 alternating with pins 38 being offset (dense packing) from the first row in a way that the second row of pins lies between the 1" pins and the ¾" pins of the first row is glued in place. The next row again contains pins 36 and 38 of alternating lengths, and so on (see FIG. 5). Then the frame is closed. The next step is to destroy the glue by heating the frame in an oven. The back plate 40 of the frame is removed and the back ends of the pins are silver soldered in a hydrogen furnace oven. The front end of the assembly is now the mold for the mask. A threaded plug on the side plate 42 is now removed and fitted with a nipple 44 to supply a pressure release medium (e.g., water) to the mold for removing the product after pouring. A suitable mold release should also be used.

To form a mask, the plastic material is poured into the mold and allowed to set. Once set, the completed mask is removed by injecting the pressure release medium, such as water, into the nipple 44 causing pressure to build up below the mask, forcing the mask from the mold.

Figure 6:
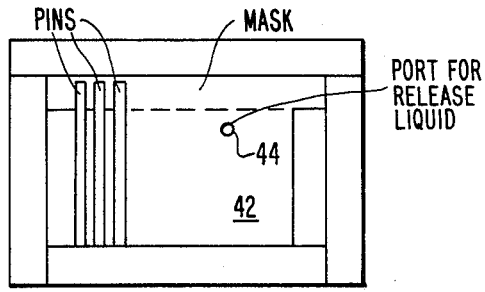
FIG. 6 shows a side elevational view of the mold of FIG. 5.

Alternatively, a mold such as that shown in FIGS. 5 and 6 can be used in a conventional injection molding machine to mass produce masks.

The transition from the 5 micrometer fiber plane to the 50 micrometer fiber plane (as in FIG. 2) can also be accomplished with a coherent fiber bundle. Starting from coherent stock which is ordinarily used to produce a rigid fiber optic image conduit consisting of soft glass fibers, rigidly fused together into a rod, one end of such a rod is drawn by a factor of 5–10. After the drawing process, both ends are polished.

The resulting product still has a point-by-point correlation between entrance and exit plane. The fiber ends on the entrance plane are now 5 micrometers (densely packed) in diameter while the fiber ends on the exit plane are 50 micrometers (also densely packed) in diameter.

This configuration will be referred to below as a "Pseudo-Lens". It acts like a lens, although it is not a lens. If the entrance plane is brought in contact with an object (e.g., a letter on a piece of paper) with the exit plane, the image of the object will appear reduced by a factor of 10 on the entrance plane again perfectly focussed.

From the foregoing, it can be seen that there are many features of the invention which enable it to be used in many applications.

The invention can be used to transport an image in total (non-scanning) in a fiber optics bundle having individual fibers of sufficient diameter (50 micrometers) to guarantee mechanical integrity; at the same time a resolving power of 5 micrometers or better is achieved by drawing out the fibers at the input end that each individual fiber now has a 5 micrometer diameter, or by using the pseudo-lens as an input device.

The drawing out process is either done collectively at the (randomly oriented) input end of the bundle or the bundle is assembled from individual fibers which have drawn out ends. Such an assembly would also consist of randomly oriented fibers.

If the pseudo-lens is used, the randomly oriented input end of the flexible bundle will consist now of 50 micrometer fibers (a polished flat end) and will be butted against the polished output end of the pseudo-lens (which is ordered). The output end of the fiber bundle will be divided into sub-bundles.

The individual fibers in the sub-bundles are terminated in masks which mate each individual fiber to its own individual detector. This mating procedure permits a 5 micrometer resolution using 50 micrometer detectors. It also permits the individual detectors to be separated from each other sufficiently without suffering a loss in resolution.

Descrambling itself is a known process for producing a coherent image from a random array of optic fibers. However, the manner in which the descrambling is achieved in the present invention is a unique computerized procedure. The input plane being random, by projecting an orthogonal grid (or a set of concentric circles with radii) onto the input plane, a matrix of input points is so defined.

The size of the input point, depending on the application, can be chosen such that either one or more than one detector is affected at the output end by one input point. This is different from making the detectors smaller than the fiber diameter. Our detectors are larger than the fiber diameter, and yet we still can assign, if so desired, more than one detector to one individual input point. The detectors affected by one input point are not neighboring detectors. The fibers leading to these detectors are only neighboring for a short length. Therefore the effect of "cross talk" between fibers is greatly reduced.

Various applications in which the optic fiber bundle of the present invention can be readily used will now be discussed. It will be understood that these application also form part of the invention.

Figure 8:
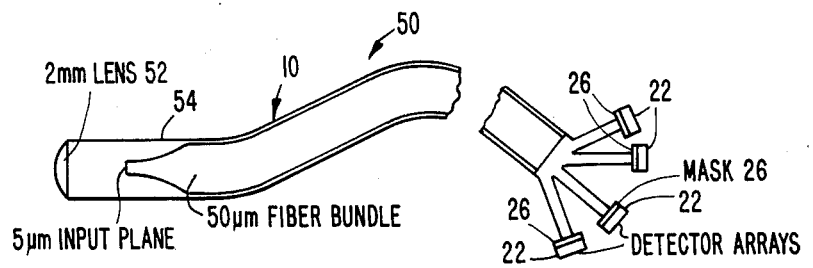
FIG. 8 shows a fiber microscope using a fiber optic bundle according to the present invention.

A fiber microscope (fiberscope) is an optical instrument made in accordance with the present invention having an objective with a short focal length, on the order of 4 mm. Since the diameter of a lens and its focal length are linked together by the f-number, such an objective lens will also have a small diameter. The present invention is ideally adapted to produce a fiberscope having an objective lens with a diameter of not more than 2 mm, e.g., for insertion into arteries, etc. FIG. 8 shows such a fiberscope 50 using a flexible bundle 10 according to the present invention. The fiberscope has an objective lens 52 mounted in a catheter sheathing 54. The objective lens 52 is 2 mm in diameter. With f/2, a focal length of 4 mm is obtained. The lens 52 is focussed on the input end of the fiber bundle 10. The image obtained by the lens 52 cannot be larger in diameter than 2 mm due to the imposed space constraint of the catheter sheathing. Using the flexible fiber bundle 10 with 50 micrometer fibers the image obtained with the lens 52 can be transported with a 50 micrometer resolution, or a part of the image can be transported with a 5 micrometer resolution. Of course, as discussed above, the output ends of the 50 micrometer fibers have to be mated to the detector arrays 26 through masks 26 in order to conserve the 5 micrometer resolution. It should also be noted that it is possible to just butt the 50 micrometer ends against the detector arrays if smaller detectors are used. However, it is preferable to use the masks and 50 micrometer detectors.

Coherent fiber bundles may be used in the fiberscope. However, these are expensive and, for this reason, it is preferable to use an incoherent bundle and descramble the output of the detector arrays.

The human eye does not resolve 5 micrometers at reading distance, but rather 100 micrometers. Therefore, if the computer connected to the detector arrays 22 presents the information from the arrays to the observer with such a resolution (meaning each 5 micrometer object point is represented by a 100 micrometer diameter dot on the screen), the image is, in fact, magnified by a factor of 20. That is the reason why the fiberscope 50 can function as a microscope if the bundle 10 is used to transport images, but does not function as a microscope if a conventional fiber bundle is used to transport the images.

Figure 9:
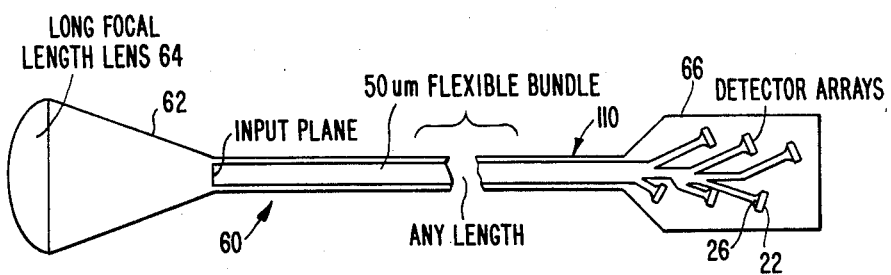
FIG. 9 shows a periscope using a fiber optic bundle according to the present invention.

The fiber bundle 10 of the present invention can also be used to produce a periscope device 60, as shown in FIG. 9. The periscope device 60 has a sheathing 62 in which the bundle 10 is mounted and also includes a lens 64 which is focussed on the input end of the bundle 10. In this application it is assumed that the required resolution on the input end of the fiber bundle 10 is 50 micrometers, but a fairly large input plane is required (e.g., 24×36 mm). This infers a large lens 64 having a long focal length. It is also assumed that the application requires images to be transported over a large distance, e.g., 100 feet. Due to the size and length of the fiber bundle, it needs to be flexible and incoherent. The approximate 260 detector arrays 22, of course, do not need to be arranged in one plane. They can be staggered and so fill the volume of a cylinder 66 as indicated in FIG. 9. In this way, the size of the receiving end of the system is still moderate. Also, the periscope sheathing can be in the form of a rigid tube or can be a flexible cable which can be rolled upon a drum. Further, as would be apparent to one of ordinary skill in the art, the lens 64 can be oriented in any direction relative to the bundle 10 as long as it remains focussed on the input end of the bundle.

Figure 10:
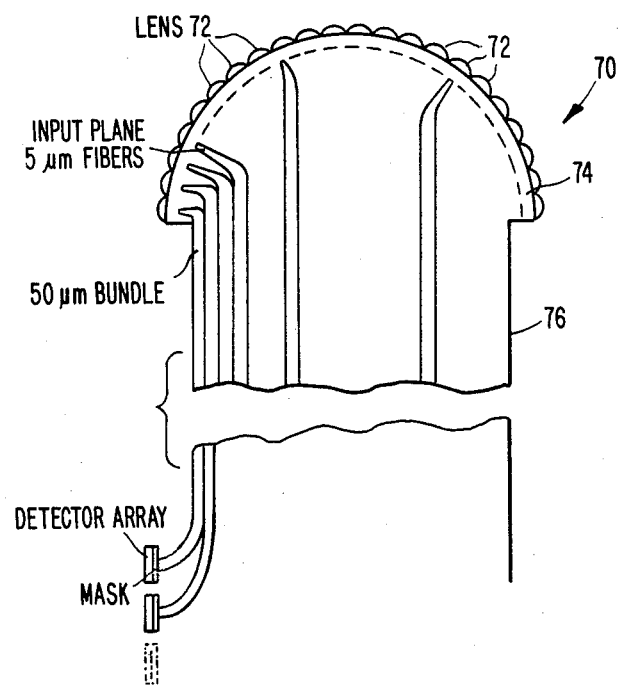
FIG. 10 shows an insects eye using an optic bundle according to the present invention.

Another application of the present invention is in the production of an insect eye type construction for producing a panoramic view. Assume there is plenty of illumination and a sentry is required which looks in all directions simultaneously (e.g., on a carrier for display of approaching aircraft). Here 10× magnification would be appreciated, so that 5 micrometer resolution on the input plane is required if a 50 micrometer output end is used. A roving (scanning) camera may be too slow to cover the total hemisphere. In an insect eye device 70 as shown in FIG. 10, a relatively small lens (2 mm) can provide the required resolution. The insect eye device comprises a plurality of individual lenses 72 which are spread over a hemispherical support 74. Each lens is focussed on one bundle 10 and the bundles 10 converge in a transport tube 76. The transfer tube 76 may penetrate a housing such as a ship's hull or the like. The resulting "dome" of lenses is of reasonable size since the input end of each bundle can be made quite small, as discussed above. The number of lenses required is very large and consequently the number of detector arrays required for read out is also large. The exact number of lenses required depends on the actual resolution required.

It would be difficult to display the data from all of the lenses at the same time. Therefore, it would be preferable to display only a small fraction of data from the detector arrays at one time. The detector arrays can be scanned to provide a moving image on a display screen. In this way, a moving target could be followed by accessing the correct arrays at the correct time. Also, it is preferable to leave gaps between the individual fields of view of the many lenses. In this way, a target would disappear and reappear periodically. Of course, the paths of the target can be predicted by a computer program based on previous path data to make sure that the correct detector array is read next, while the previous image is held on the screen until the new image appears. Since each lens stares at a certain section in space, the position of the target is easily obtainable and can be displayed on the screen. Multiple targets can be displayed on multiple screens.

Still another application of the present invention is to coat—in lieu of using an optical system—the first ends of the fiberoptic cables with a material which fluoresces under irradiation with ionizing radiation, such as x-rays, gamma rays, beta and alpha particles. A typical material may be zinc sulfide. The effect will be that the detectors on the detector arrays mated to the sub-bundle will receive visible light, the intensity of which is related to the intensity of the ionizing radiation, which irradiated the first ends of the fibers. By reading the detector arrays correctly, meaning using the look-up tables which translate input addresses to output addresses, an x-ray image can be constructed and displayed on the computer monitor, which is identical to a photographic x-ray, which one would have obtained when placing a photographic x-ray film in the input plane.

The foregoing description is set forth for the purpose of illustrating the present invention but is not intended to limit the invention. Clearly, numerous additions, substitutions and other modifications can be made to the invention without departing from the scope of the invention as set forth in the appended claims.

What is claimed is:

1. An apparatus, comprising:
   a fiber optic bundle, comprising:
   a plurality of individual optic fiber elements, each of said optic fiber elements having a first end and a second end, the first ends of said optic fiber elements being of a smaller cross sectional area than said second ends, said first ends of said optic fibers being mechanically joined to provide strength to said fiber optic bundle;
   said second ends of said optic fiber elements being connected in sub-bundles, each sub-bundle comprising more than one optic fiber;
   a light source for projecting light on said first ends of said optic fiber elements; and
   means for receiving light from the second ends of said optic fibers,
   said receiving means includes an optical detector array connected to each sub-bundle, wherein said first ends of said optic fibers are arranged randomly relative to said second ends, and wherein said receiving means includes means for descrambling light signals received by said second ends to reproduce a correct image of an image projected onto said first ends.

2. An apparatus according to claim 1 wherein said receiving means further includes an optical mask for mating the fibers of the sub-bundles to the optical detectors on said optical detector array.

3. An apparatus according to claim 1 wherein said first end of each optic fiber is at least as small as about 5 micrometers in diameter.

4. An apparatus according to claim 3 wherein said second end of each optic fiber is as large as about 50 micrometers in diameter.

5. An apparatus according to claim 1 wherein said second end of each optic fiber is at least an order of magnitude greater in diameter than said first end.

6. An apparatus according to claim 1 wherein said descrambling means comprises means for displaying a matrix of lines, the intersections of which define addresses of input points on said first ends of said optic fibers.

7. An apparatus according to claim 1 including a lens focussed on said first ends of said fibers.

8. An apparatus according to claim 7 wherein said lens and said fiber optic bundle are contained in a catheter sheathing.

9. An apparatus according to claim 7 wherein said lens and said fiber optic bundle are contained in a periscope tube.

10. An apparatus according to claim 1 including a plurality of fiber optic bundles and a plurality of lenses focussed, respectively, on said fiber optic bundles, said lenses being positioned over a hemisphere.

11. A method of making optic fiber bundles, comprising:
providing a plurality of optic fibers, each having a first end and a second end;
mechanically connecting the first ends of said optic fibers to form a fiber bundle;
reducing the cross section of the first end of each optic fiber relative to its second end; and
connecting said second ends of said optic fibers into sub-bundles having more than one second end each, wherein an image is projected on the first end to be sensed at the second end and wherein the step of mechanically connecting said first ends of said optic fiber bundles comprises connecting them such that the orientation of said first ends is random relative to said second ends, further including the step of descrambling the sensed image at said second ends.

12. The method according to claim 11 wherein said step of descrambling comprises displaying a matrix of lines, the intersections of which define addresses of input points from said first ends of said optic fibers.

13. An apparatus, comprising:
a fiber optic bundle, comprising:
a plurality of individual optic fiber elements, each of said optic fiber elements having a first end and a second end, said first ends of said optic fiber elements being arranged randomly relative to said second ends, the first ends of said optic fiber elements being of a smaller cross sectional area than said second ends,
wherein the second ends of said optic fiber elements are connected in random sub-bundles, each comprising more than one optic fiber element end, the optic fiber element second ends in each sub-bundle being randomly arranged relative to the optic fiber element first ends;
means for projecting an image onto the first ends of the optic fiber elements; and
means for receiving light from the second ends of said optic fiber elements in all of said sub-bundles, including means for descrambling light signals received by all of said sub-bundles to reproduce the image projected onto said first ends.

14. An apparatus according to claim 13 wherein said receiving means includes an optical detector array containing a plurality of optical detectors connected, respectively, to said sub-bundles.

15. An apparatus according to claim 14 wherein said receiving means further includes an optical mask for mating the optic fiber elements of the sub-bundles to the optical detectors on said optical detector array.

16. An apparatus according to claim 13 wherein said optic fiber element first ends are arranged in sub-bundles, the sub-bundles of optic fiber element first ends being random relative to the sub-bundles of optic fiber second ends.

* * * * *